United States Patent [19]

Rappoport et al.

[11] Patent Number: 5,156,630
[45] Date of Patent: Oct. 20, 1992

[54] ANKLE JOINT PROSTHESIS FIXABLE IN MORE THAN ONE ORIENTATION

[75] Inventors: Albert F. Rappoport, Santa Monica, Calif.; Samuel C. Shawe, Bend, Oreg.; Michael R. Ross, Leucadia, Calif.

[73] Assignee: Rampro, Inc., Santa Monica, Calif.

[21] Appl. No.: 697,884

[22] Filed: May 9, 1991

[51] Int. Cl.⁵ .............................................. A61F 2/66
[52] U.S. Cl. ..................................... 623/47; 623/38; 602/27; 403/103; 403/350
[58] Field of Search .................... 623/47-52, 623/38, 53-56; 128/80 E, 80 F, 80 H; 602/16, 27, 28; 403/103, 106, 350, 351, DIG. 8

[56] References Cited

U.S. PATENT DOCUMENTS

| | | | |
|---|---|---|---|
| 911,243 | 2/1909 | Johannesen | 128/80 F |
| 2,749,557 | 6/1956 | Riddle | 623/50 |
| 3,419,227 | 12/1968 | Werkmeister et al. | 403/350 X |
| 3,480,972 | 12/1969 | Prahl | 623/50 |
| 4,413,360 | 11/1983 | Lamb et al. | 623/47 |
| 4,865,611 | 9/1989 | Al-Turaiki | 623/38 |

FOREIGN PATENT DOCUMENTS

| | | | |
|---|---|---|---|
| 0016268 | 10/1980 | European Pat. Off. | 128/80 F |
| 2110806 | 10/1971 | Fed. Rep. of Germany | 403/351 |
| 0262319 | 1/1970 | U.S.S.R. | 623/47 |
| 0381347 | 5/1973 | U.S.S.R. | 623/53 |
| 1509641 | 5/1978 | United Kingdom | 128/80 F |
| 2177925 | 2/1987 | United Kingdom | 623/47 |

Primary Examiner—David Isabella
Assistant Examiner—D. Willse
Attorney, Agent, or Firm—Cislo & Thomas

[57] ABSTRACT

An ankle joint prosthesis comprises an upper part for attachment to an artificial leg and a lower part for attachment to an artificial foot, with the upper and lower parts rotatively coupled and capable of being fixed in a first position for walking, a second position for swimming, or a free-flexing mode for activities such as skiing or rowing. The upper and lower ankle parts have coaxial bores in which a cam part is mounted by means of two bushings. A pin-and-slot arrangement allows locking of the prosthesis in a desired position. Changing positions takes only seconds, and is effected by rotating a spring-loaded "D"-ring on the side of the ankle prosthesis by hand. In a preferred embodiment the ankle joint prosthesis is completely waterproof and precision machined from a lightweight, high-strength plastic.

17 Claims, 4 Drawing Sheets

ANKLE JOINT PROSTHESIS FIXABLE IN MORE THAN ONE ORIENTATION

BACKGROUND OF THE INVENTION

1. Field of the Invention

The invention relates generally to joint prostheses, and more particularly to an ankle joint prosthesis that can be set in either of two fixed positions for walking and swimming, respectively, or a free-flexing mode suitable for activities such as skiing or rowing.

2. Description of the Related Art

The following patents may be relevant to the present invention:

| Patent No. | Inventor | Issue Date |
|---|---|---|
| 667,511 | I. R. Fenner et al. | February 5, 1901 |
| 1,123,928 | J. F. Rowley | January 5, 1915 |
| 2,617,115 | E. C. Ellery | November 11, 1952 |
| 2,692,990 | E. R. Schaefer | November 2, 1954 |
| 2,749,557 | G. P. Riddle | June 12, 1956 |
| 3,480,972 | G. Prahl | December 2, 1969 |
| 3,546,712 | M. C. Tarte | December 15, 1970 |
| 3,597,767 | J. Prahl | August 10, 1971 |
| 3,649,968 | J. Prahl | March 21, 1972 |
| 3,800,333 | K. A. Frieberg | April 2, 1974 |
| 4,283,800 | M. T. Wilson | August 18, 1981 |
| 4,413,360 | S. R. Lamb et al. | November 8, 1983 |

U.S. Pat. No. 2,749,557 to Riddle is directed to an adjustable ankle joint for use on an artificial limb. The ankle portion 13 of artificial limb 11 pivotally couples the foot portion 14 to the leg portion 12 by means of pins or studs 15. The angular position of the foot portion relative to the leg portion is lockingly maintained in angular relationship by means of a locking rod 24 which passes through the pivoted ankle joint for coupling with one of a plurality of recesses 39 formed in member 20 of foot portion 14. The locking rod is operated by means of a lever 28.

U.S. Pat. No. 3,546,712 to Tarte is directed to an artificial leg having means for retaining the joint in a relatively locked condition. The knee joint pivotally couples the upper leg element and the lower leg element by means of the pin 18. The joint is lockable by means of the rod 22 which extends from the foot element 16 into the upper leg element 12. When the end 24 of rod 22 is captivated within the socket 31 of upper leg 12, the knee joint is locked, preventing pivotal movement. However, the pin of rod 22 is engaged from the socket 31 by lifting the leg, allowing the heel 46 to drop, thereby allowing the rod to withdraw from the socket.

U.S. Pat. No. 4,413,360 to Lamb et al. is directed to an adjustable prosthetic ankle having a pivotable foot portion which may be secured in a desired position. The ankle assembly comprises an ankle member 16 which adjustably couples a foot member 18 to a shin member 14. The ankle member 16 is pivoted with a mechanism 20 comprising a yoke 24 pivotally coupled to a rocker block 46. The pivotal coupling is provided by two cross rocker block 46. The pivotal eccentrically positioned clamp holes 36 and through a pair of cylindrical pivot inserts 38 which flex and clamp around cross pins 34 when the adjustment mechanism is tightened by the user. Clamping screws 38 may be tightened to a locking position of the ankle joint.

U.S. Pat. No. 1,123,928 to Rowley is directed to an ankle joint for use with an artificial limb. The upper block comprises a threaded shank 1 having a pair of arms 3 terminating in a pair of co-axially aligned cylinders 4 formed in one end. The lower block comprises a bearing member 5 coupled with a threaded shank 10, while the cylinders 4 of the upper block are coupled to the bearing member 5 for pivotal coupling therebetween. No means for locking the position of the ankle is provided.

U.S. Pat. No. 2,617,115 to Ellery is directed to an ankle joint for artificial limbs. The ankle joint 15 includes an upper block 16 pivotably coupled to a lower block 17 by means of the pivot pin 32. No means for adjustably locking the position of the joint is provided.

Although each of the ankle joint prostheses discussed above possesses certain desirable features, all suffer from one or more deficiencies. Most conventional ankle joint prostheses are designed primarily for walking and do not allow the position of the foot to be changed for different activities. Or, if an ankle prosthesis is designed to be adjustable, the adjustment requires a special tool or cannot be made rapidly and conveniently. Special sports prostheses have been designed, but these are usually for one particular type of athletic activity, and a person must switch to a different special prosthesis to engage in a different sport.

There has been a long-felt need for an ankle joint prosthesis which can be used for a range of different activities, can be quickly and easily adjusted from one position to another, and which is lightweight, strong, and waterproof. To date, although several attempts have been made by numerous other skilled inventors to achieve all of these desirable operational capabilities, no ankle joint prosthesis has been designed or built that has satisfied the necessary criteria.

SUMMARY OF THE INVENTION

With the deficiencies of the previously known ankle joint prostheses clearly in mind, applicants have invented an ankle joint prosthesis comprising an upper part for attachment to an artificial leg and a lower part for attachment to an artificial foot, with the upper and lower parts rotatively coupled and capable of being fixed in a first position for walking, a second position for swimming, or a free-flexing mode for activities such as skiing or rowing. The upper and lower ankle parts have coaxial bores in which a cam part is mounted by means of two bushings. A pin-and-slot arrangement allows locking of the prosthesis in a desired position or allowing relative rotation of the upper and lower parts. Changing positions takes only seconds, and is effected by rotating a spring-loaded "D"-ring on the medial side of the ankle prosthesis by hand. In a preferred embodiment the ankle joint prosthesis is completely waterproof and precision machined from a lightweight, high-strength plastic. The ankle joint prosthesis of the invention can be worn covered with a special scuba diving bootie to prevent sand or other foreign particles from entering the mechanism.

Accordingly, it is an object of the present invention to provide an ankle joint prosthesis which allows a broader range of motion when swimming, skiing, and rowing.

It is another object of the present invention to provide an ankle joint prosthesis that has a unique locking mechanism that can be switched within seconds from a walking position to a plantar flexed position for swimming or a free flexing position for skiing and rowing.

It is still another object of the present invention to provide an ankle joint prosthesis which can be used with below-knee, above-knee, and bilateral prostheses.

It is yet another object of the present invention to provide an ankle joint prosthesis which is compatible with most endo- and exoskeletal designs.

It is one more object of the present invention to provide an ankle joint prosthesis which can function in an anatomically normal ankle position when mounted inside a low-profile foot.

It is a further object of the present invention to provide an ankle joint prosthesis which in a preferred embodiment is made of water-proof materials, weighs only 9 ounces, and is constructed with a special light-weight, high-strength plastic.

It is yet another object of the present invention to provide an ankle joint prosthesis for which one size fits all.

It is an additional object of the present invention to provide an ankle joint prosthesis which allows active participation in a wide range of sports activities and eliminates the need for more than one sports prosthesis.

One more object of the present invention is to provide an ankle joint prosthesis which allows the person who scuba dives or swims to walk to the water's edge and then lock the ankle into a plantar flexed position so that the toes are pointed down in a natural swimming position, which enables the swimmer to generate an increased level of power during the kicking motion.

Yet another object of the present invention is to provide an ankle joint prosthesis which has a free-flexing position that makes skiing and rowing more accessible to people using prostheses.

Still another object of the present invention is to provide an ankle joint prosthesis which can be used with the patient's existing prosthesis or incorporated into a newly designed recreational prosthesis.

Finally, it is an object of the present invention to provide an ankle joint prosthesis which is a prosthetic sports ankle that functions in a plurality of fixed positions or in a free-flexing mode.

BRIEF DESCRIPTION OF THE DRAWINGS

The various objects, features, desirable attributes, and advantages of the ankle joint prosthesis of the present invention will become apparent in light of the following detailed description taken together with the accompanying drawings, in which.

DETAILED DESCRIPTION OF THE PREFERRED EMBODIMENT

Figure 1:
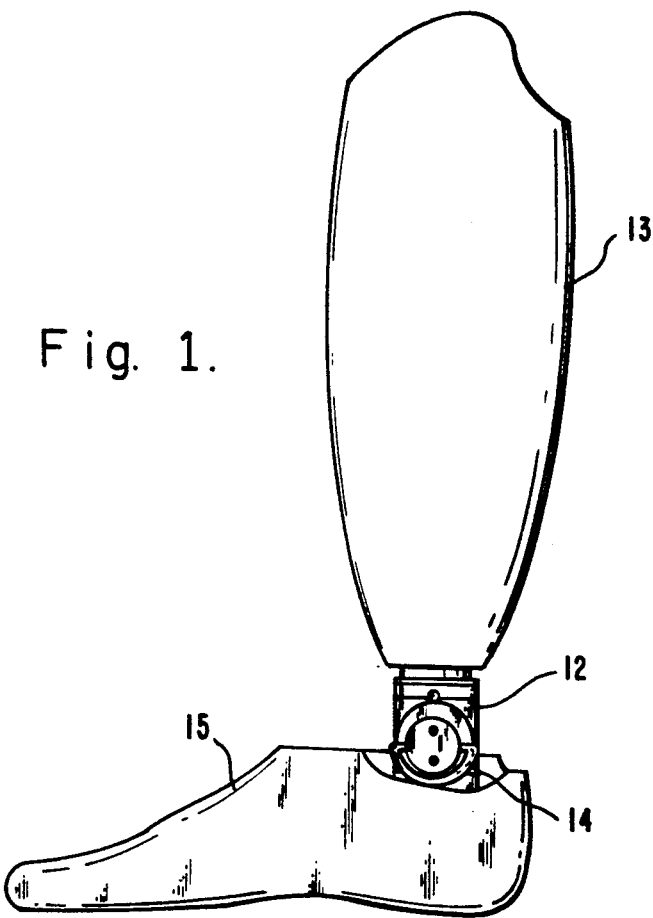
FIG. 1 is a side view of an ankle joint prosthesis in accordance with the principles of the invention attached to and serving as the connection between an artificial right foot and an artificial right leg.

Referring to FIG. 1, a right-side embodiment of an ankle joint prosthesis 10 of the invention is shown in a side view, with an upper ankle part 12 attached to an artificial leg 13 and a lower ankle part 14 attached to an artificial foot 15.

Figure 2:
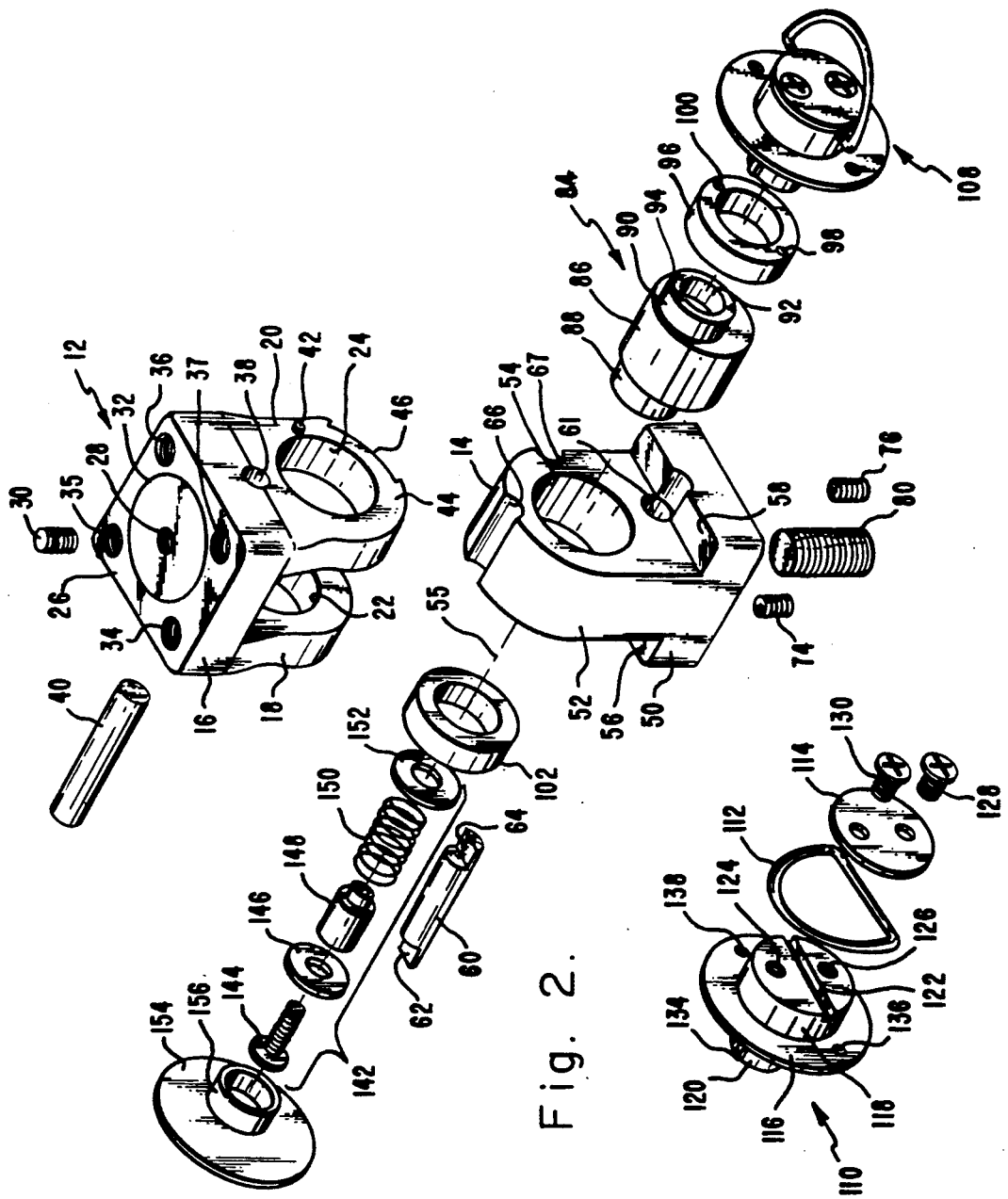
FIG. 2 is a perspective exploded view of the ankle joint prosthesis of FIG. 1.

Referring in detail to FIG. 2, in which a left-side embodiment of ankle joint prosthesis 10 is illustrated in an exploded perspective view, upper ankle part 12 comprises a generally square top part 16, from which first and second generally disk-shaped posts 18 and 20 depend. Posts 18 and 20 have circular bore holes 22 and 24 therethrough, respectively.

Top part 16, on an upper face 26, has a central hole 28 which is tapped to accept a set screw 30, and a concentric circular groove 32. There are four tapped holes 34, 35, 36, and 37 near the corners of face 26 of top part 16. A through-hole 38 at the juncture of top part 16 with posts 18 and 20 accepts an upper dowel 40 in a press fit. Approximately half the cross sectional area of upper dowel lies above a flat lower face (not seen in FIG. 2) of top part 16 between first post 18 and second post 20. A handle-locking pin 42 is press fitted into a blind hole in a medial end face 44 of second post 20 and extends above the surface of end face 44. Near pin 42 there is a reduced-diameter segment 46 of second post 20 over approximately a quarter of its circumference. First post 18 has a matching reduced-diameter segment 48 over a corresponding part of the circular outer periphery of post 18.

Lower ankle part 14 comprises a generally square base part 50 from which a generally circular central bearing post 52 extends upwardly. A borehole 54 has an axis 55 in a plane parallel to first and second upper shoulder portions 56 and 58 which lie on either side of bearing post 52.

First and second upper shoulder portions 56 and 58 are flat. A cylindrical lower dowel 60 is press-fitted into a lower dowel hole 61 located on an axis parallel to axis 55, and lying approximately on the flat surfaces of shoulder portions 56 and 58.

Lower dowel 60 has first and second flattened upper portions 62 and 64 which fit against reduced-diameter segments 46 and 48 of first and second posts 18 and 20, respectively, when ankle joint prosthesis 10 is assembled. There is a first semicylindrical slot 66 in the topmost portion of bearing post 52 into which upper dowel 40 can fit when ankle joint prosthesis 10 is assembled and it is desired to lock prosthesis 10 into a first fixed position in which the relative orientations of upper ankle part 12 and lower ankle part 14 are such as to accommodate walking.

There is a second semicylindrical slot 67 parallel to and approximately 75 to 90 degrees away from first slot 66 on the outer periphery of bearing post 52 into which upper dowel 40 can fit when ankle joint prosthesis 10 is assembled and it is desired to lock prosthesis 10 into a second fixed position in which the relative orientations of upper ankle part 12 and lower ankle part 14 are such as to accommodate swimming, with the artificial foot 15 in a plantar flexed position.

Figure 3:
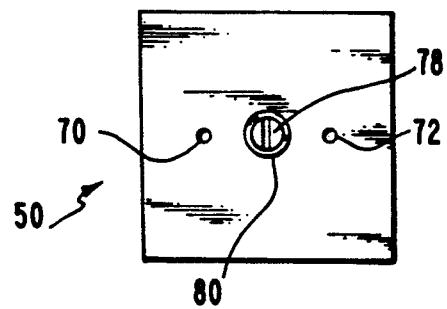
FIG. 3 is a bottom plan view of the lower ankle part shown in FIG. 2.

Referring to FIG. 3 bottom end face of base part 50 has first and second tapped holes 70 and 72 near midpoints of opposite sides of end face 68 on a line bisecting the area of end face 68 to accommodate first and second lower ankle part set screws 74 and 76, respectively. A central tapped hole 78 in bottom end face 68 of base part 50 has a threaded and tapped metal sleeve 80 screwed into it.

Referring again to FIG. 2, cam 84 has a center cylindrical part 86 of width to match the spacing between first and second posts 18 and 20, and of a diameter to match borehole 54. To either side of center part 86 extend first and second cylindrical bushing seats 88 and 90 with a hole 92 therethrough that has a smaller diameter at the medial end of cam 84 than at the lateral end. Hole 92 is offset from the central axis of center cylindrical part 86 and has a rectangular keyway 94 with a depth shallower than a width.

Cam 84 is used to join upper ankle part 12 (attached to artificial leg 13) with lower ankle part 14 (attached to artificial foot 15) by insertion of center part 86 through boreholes 22, 54, and 24. A medial bushing 96 fits over second bushing seat 90 and inside second circular bore hole 22.

Medial bushing 96 has first and second screw holes 98 and 100 which are tapped to facilitate extraction of bushing 96 with a bushing puller. A lateral bushing 102 fits over first bushing seat 8 and inside first circular bore hole 22. Lateral bushing 102 has first and second screw holes 104 and 106 on a lateral end face (not shown) which are tapped to facilitate extraction of bushing 102 with a bushing puller.

Handle assembly 108 comprises a cam actuator 110, a "D"-ring 112, and a "D"-ring cap 114. Cam actuator 110 has a middle disk-shaped portion 116 from which a first cylindrical part 118 of smaller diameter projects medially and a second cylindrical part 120 of even smaller diameter projects laterally.

The medial end face of first cylindrical part 118 of cam actuator 110 has a shallow semicylindrical slot 122 along a diameter with first and second tapped holes 124 and 126. The straight portion of "D"-ring 112 is held in slot 122 by "D"-ring cap 114, which is attached to cam actuator 110 by first and second screws 128 and 130.

Figure 4:
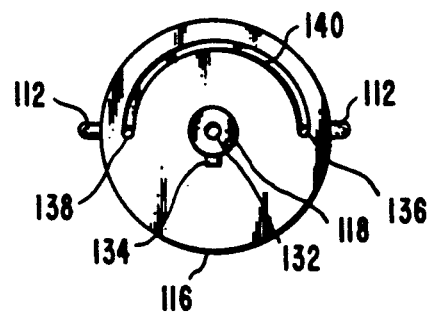
FIG. 4 is a left side elevational view of a cam actuator shown in FIG. 2.

As shown in FIG. 4, second cylindrical part 120 has a central tapped hole 132 and a Woodruff key 134 which fits keyway 94 in hole 92 of cam 84. There are first and second pin holes 136 and 138 through disk-shaped portion 116 near opposite ends of a diameter, and these are joined by a semicircular slot 140 in the lateral face of portion 116.

Referring again to FIG. 2, cam actuator 110 is inserted into medial bushing seat 90 of cam 84 so that Woodruff key 134 is in keyway 94 and handle-locking pin 42 is in semicircular slot 140. Handle assembly 108 is retained inside cam 84 in a spring-loaded fashion by spring-loading subassembly 142, consisting of screw 144, first washer 146, sleeve 148, spring 150, and second washer 152. Spring 150, sandwiched between first and second washers 146 and 152, fits around sleeve 148 which in turn fits on screw 144. Screw 144 is partly screwed into central tapped hole 132 of second cylindrical part 120 of cam 84 to provide sufficient spring tension to hold handle-locking pin in pin hole 136 or 138.

When "D"-ring 112 is pulled in a medial direction against the tension of spring 150, cam actuator 110 is disengaged from handle-locking pin 42 and is then free to rotate cam 84 while pin 42 moves in semicircular slot 140. An end cap 154 has a central hub 156 which is a tight fit inside the inner bore of bushing seat 88.

It should be noted that although handle assembly 108 in the embodiment described above is mounted on the medial side of ankle prosthesis 10, handle assembly 108 could be mounted on the lateral side of prosthesis 10 in an alternative embodiment. The alternative mounting embodiment is easily accomplished by reversing cam 86 in bore-holes 22, 54, and 24. Handle assembly 108 is then switched to the lateral side of upper ankle part 12 and spring-loading assembly 142 is switched to the medial side of upper ankle part 12. Ultimately it is a matter of choice for the wearer whether medial or lateral mounting of handle assembly 108 is more convenient.

In a preferred embodiment of ankle joint prosthesis 10, most parts, including upper ankle part 12, lower ankle part 14, bushings 96 and 102, cam 84, cam actuator 110, "D"-ring cap 114, and end cap 154 are all made of a lightweight but strong plastic such as DuPont Delrin. The metal parts of ankle joint prosthesis 10, such as the various screws, upper dowel 40, pin 42, lower dowel 60, and "D"-ring 112 are preferably made of corrosion resistant materials.

OPERATION OF THE INVENTION

To unlock ankle prosthesis 10 "D"-ring handle 112 is grasped, pulled out approximately ⅛", and rotated (clockwise for a right ankle, counterclockwise for a left ankle). Once handle 112 has been rotated slightly, it is no longer necessary to continue to pull handle 112. Handle 112 is rotated 180 degrees.

When handle assembly 108 engages handle locking pin 42, ankle prosthesis 10 is unlocked. If handle assembly 108 is not rotated a full 180 degrees and engaged on handle locking pin 42, the mechanism of ankle prosthesis 10 will bind when the foot 15 is repositioned.

To position foot 15 it is moved to the desired walk or swim position. A slight resistance in the ankle mechanism will be felt when moving foot from one position to another. When resistance ceases, the ankle mechanism is ready to lock.

To lock the ankle mechanism "D"-ring handle 112 is grasped, pulled out approximately ⅛", and rotated (counterclockwise for a right ankle, clockwise for a left ankle). Again, once handle 112 has been rotated slightly, it is no longer necessary to continue to pull handle 112. Handle 112 is rotated 180 degrees, and when handle assembly 108 engages handle locking pin 42 the ankle mechanism is locked.

It is absolutely necessary that the ankle prosthesis be locked before walking is attempted. If the ankle prosthesis is not locked, damage to the ankle prosthesis and/or bodily injury may occur.

If handle 112 will not rotate a full 180 degrees to the locked position (handle 112 should not be forced), handle 112 should be turned back to the unlocked position, foot 15 should be repositioned slightly, and handle 112 should be rotated once again to the locked position. It is necessary for foot 15 to be relatively close to either the walk or swim position so that the ankle prosthesis 10 may lock.

If the foot 15 is not properly positioned when attempting to lock ankle prosthesis 10, binding will occur. If after foot 15 is properly positioned, ankle prosthesis 10 still will not lock, handle 112 should be turned to the unlocked position and a check between upper and lower ankle parts 12 and 14 should be made for foreign objects. The present invention is not tolerant to sand or dirt. It is recommended that a diving bootie with a full-length zipper be used to cover ankle prosthesis 10 in sandy areas.

The present invention provides an ankle joint prosthesis which within seconds can be switched from the walking position to an extended position for swimming, or a free-flexing position for skiing and rowing. When used with a proper suspension system, the present invention allows amputees to achieve new levels of athletic performance.

Figure 5:
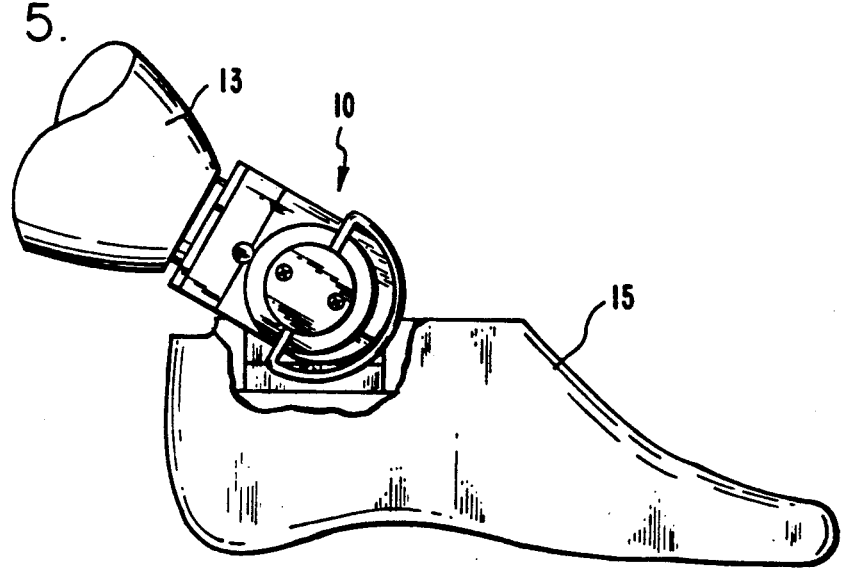
FIG. 5 is a side view of the left ankle joint prosthesis of FIG. 2 locked into a plantar flexed position suitable for swimming.
Figure 6:
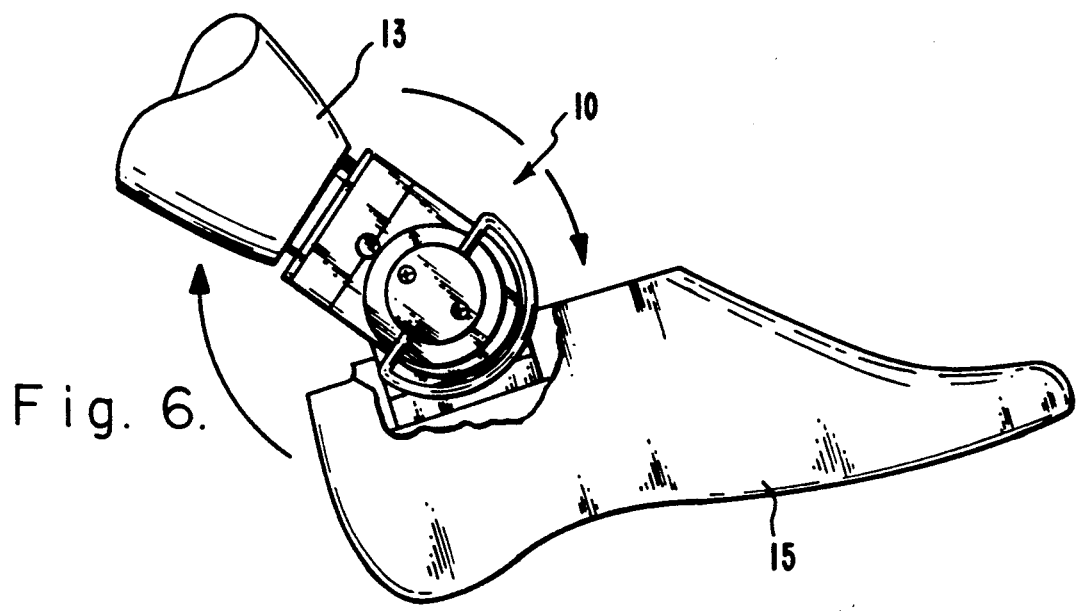
FIG. 6 is a side elevational view of the left ankle joint prosthesis of FIG. 2 in a free-flexing mode suitable for skiing or rowing.
Figure 7:
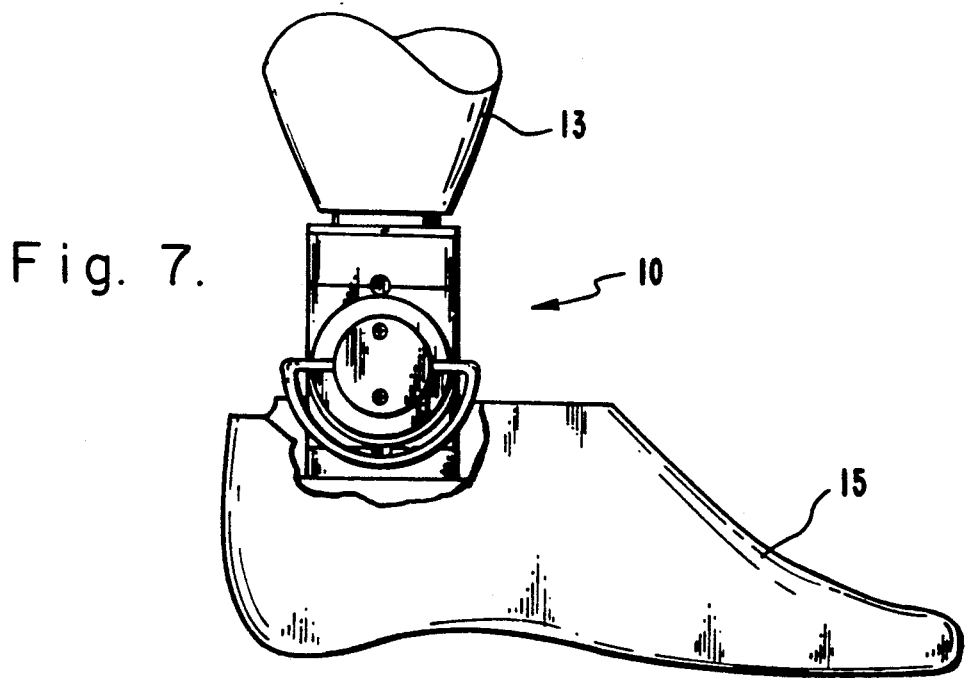
FIG. 7 is a side view of the left ankle joint prosthesis of FIG. 2 locked into a position suitable for walking.

FIG. 5 depicts ankle joint prosthesis 10 locked in a plantar flexed position for swimming. As shown in FIG. 6, ankle joint prosthesis 10 can operate in a free-flexing mode for activities such as skiing or rowing. In the free-flexing mode depicted in FIG. 6, upper ankle part 12 and lower ankle part 14 are free to rotate with respect to each other subject to the friction between lower ankle part 14 and center part 86 of cam 84 and between the medial and lateral end faces of bearing post 52 with the abutting interfaces of first and second posts 18 and 20. FIG. 7 shows ankle joint prosthesis 10 locked into a position suitable for walking, with upper ankle part 12 and lower ankle part 14 making an angle of approximately 180 degrees with respect to each other. The unique locking mechanism of the present invention eliminates the need for more than one sports prosthesis. Conventional prostheses do not permit the range of natural ankle positions required for some sports. As a result, active amputees are handicapped by existing designs.

The present invention may be used in the unlocked position for other activities which require a range of ankle-joint motion similar to snow skiing or rowing. With the present invention an amputee is able to achieve the natural movements necessary to engage in athletic activities the way the amputee used to.

The present invention can often be used with a patient's existing prosthesis. It is compatible with most endoskeletal designs, and can function in an anatomically normal ankle position when mounted inside a low-profile foot. The present invention in a preferred embodiment weighs about 9 ounces, is completely waterproof, and is precision-machined from a special lightweight, high-strength plastic.

The above-described embodiments are furnished as illustrative of the principles of the invention, and are not intended to define the only embodiments possible in accordance with our teaching. Various minor modifications and variations will occur to those ordinarily skilled in the art. For example, parts of the prosthesis might be machined out of a lightweight corrosion-resistant metal or injection molded from a suitable plastic. Also, the exact shapes of certain parts are not crucial, and alternative ways of achieving certain mechanical functions of the invention may be envisioned. The locking of upper ankle part 12 and lower ankle part 14 in fixed positions could be accomplished in different ways. For example, the insertion of various types of locking pins into properly aligned holes would have the advantage of providing a quick-release mechanism in combination with a cable attached to the end of the pin. The cable could be used to pull out the pin to effect the transition from a fixed position to a free-flexing mode. The invention is to be considered as encompassing not only the specific embodiments shown, but also any others falling within the scope of the following claims.

We claim:

1. An ankle joint prosthesis for connecting an artificial leg with an artificial foot, comprising:
   an upper ankle part;
   a lower ankle part;
   intermediate means joining said upper ankle part with said lower ankle part for rotating said upper and lower ankle parts with respect to each other, selectively locking said prosthesis into a first fixed relative orientation of said upper and lower ankle parts, and selectively locking said prosthesis into a second fixed relative orientation of said upper and lower ankle parts;
   wherein said intermediate means includes hand-operable means for selecting said first fixed relative orientation, said second fixed relative orientation, or a condition of freedom of relative rotation between said upper and lower ankle parts;
   wherein said upper ankle part comprises an upper part with spaced-apart medial and lateral descending parts, each having a coaxial through-hole of the same first diameter; and said lower ankle part comprises a base part with a centered semicylindrical ascending part fitting between said medial and lateral descending parts of said upper ankle part and having a through-hole with a diameter equal to that of each said coaxial through-hole in said upper ankle part;
   wherein said intermediate means includes a hollow cylindrical connector with a central part of an outer diameter fitting said through-hole of said lower ankle part and mounted therein, having to either side of said central part first and second eccentrically located hollow cylindrical portions with outer diameters equal to a second diameter, mounted in said coaxial through-holes of said medial and lateral descending parts of said upper ankle part by means for first and second bushings having outer diameters equal to said first diameter and inner diameters equal to said second diameter;
   rotation means for rotating said cylindrical connector inside said upper ankle part;
   lock means for locking said rotation means to said upper ankle part;
   first engagement means for engaging said upper ankle part with said lower ankle part in a first relative orientation; and
   second engagement means for engaging said upper ankle part with said lower ankle part in a second relative orientation;
   wherein said ankle joint prosthesis can be fixed in a first relative orientation of said upper and lower ankle parts when both said first engagement means and said lock means are employed, and in a second fixed relative orientation of said upper and lower ankle parts when both said second engagement means and said lock means are employed, and in a configuration allowing relative rotating of said upper and lower ankle parts with respect to each other when only said lock means is employed.

2. The ankle joint prosthesis of claim 1 wherein said rotation means comprises:
   a cam actuator having a cylindrical lateral end matching an inner diameter of said second eccentrically located hollow cylindrical portion and mounted therein, said cylindrical lateral end having a key thereon fitting a keyway inside said second eccentrically located hollow cylindrical portion, said cam actuator having a medial end;
   spring-loading means for holding said cam actuator inside said second eccentrically located hollow cylindrical portion under spring tension; and
   handle means on said medial end of said cam actuator for pulling said actuator in a medial direction and rotating said actuator.

3. The ankle joint prosthesis of claim 2 wherein said spring-loading means comprises:
   an end cap fitting over a lateral end of said lateral descending part, with a central through hole therein;
   a helical spring;
   a hollow sleeve inside said spring;
   first and second washers disposed at first and second ends of said spring;
   a screw passing through said central through-hole of said end cap, threaded through said first washer, said sleeve and spring, and said second washer, inserted into said cam actuator and screwed into a tapped central hole in said lateral end of said cam actuator;
   wherein tightening or loosening of said screw adjusts a spring tension which holds said cam actuator against said medial descending part of said upper ankle part.

4. The ankle joint prosthesis of claim 2 wherein said handle means comprises a "D"-ring attached to said medial end of said cam actuator.

5. The ankle joint prosthesis of claim 1 wherein said lock means comprises:
   a projection from a medial end face of said medial descending part of said upper ankle part;
   wherein a medial end face of a cam actuator has first and second diametrically opposed holes each shaped complementarily to said projection, said holes being connected by a shallow semicircular slot in lateral end face of a central annular flange on said cam actuator, and said actuator can be rotated to position said projection in either of said diametrically opposed holes.

6. The ankle joint prosthesis of claim 1 wherein said first engagement means comprises:
   a projection between said lateral and medial descending parts along an axis parallel to said coaxial through-holes; and
   a first slot complementary in shape to said projection, centrally located on said centered ascending part along an axis parallel to said through-hole in said lower ankle part;
   wherein said upper ankle part engages said lower ankle part when said upper and lower parts are oriented at approximately 180° with respect to each other and a cam actuator is rotated fully clockwise for a left-ankle embodiment and fully counterclockwise for a right-ankle embodiment.

7. The ankle joint prosthesis of claim 1 wherein said second engagement means comprises:
   a projection between said lateral and medial descending parts along an axis parallel to said coaxial through-holes; and
   a second slot complementary in shape to said projection, located approximately 75 to 90 degrees away from a first slot between said first slot and said base part of said lower ankle part along an axis parallel to said through-hole in said lower ankle part;
   wherein said projection is engaged by said second slot when said upper and lower ankle parts are oriented at approximately 90 to 105 degrees with respect to each other and said cam actuator is rotated fully clockwise for a left-ankle embodiment and fully counterclockwise for a right-ankle embodiment.

8. The ankle joint prosthesis of claim 1 wherein said upper ankle part further comprises first attachment means for attaching said upper ankle part to said artificial leg and said lower ankle part further includes second attachment means for attaching said lower ankle part to said artificial foot.

9. An ankle joint prosthesis for connecting an artificial leg with an artificial foot, comprising:
   an upper ankle part including an upper part with spaced-apart medial and lateral descending parts, each having a coaxial through-hole of the same first diameter;
   a lower ankle part including a base part with a centered semicylindrical ascending part fitting between said medial and lateral descending parts of said upper ankle part and having a through-hole with a diameter equal to that of each said coaxial through-hole in said upper ankle part;
   intermediate means including a hollow cylindrical connector with a central part of an outer diameter fitting said through-hole of said lower ankle part and mounted therein, having to either side of said central part first and second eccentrically located hollow cylindrical portions with outer diameters equal to a second diameter, mounted in said coaxial through-holes of said medial and lateral descending parts of said upper ankle part by means of first and second bushings having outer diameters equal to said first diameter and inner diameters equal to said second diameter;
   rotation means for rotating said cylindrical connector inside said upper ankle part;
   lock means for locking said rotation means to said upper ankle part;
   first engagement means for engaging said upper ankle part with said lower ankle part in a first relative orientation; and
   second engagement means for engaging said upper ankle part with said lower ankle part in a second relative orientation;
   wherein said ankle joint prosthesis can be fixed in a first relative orientation of said upper and lower ankle parts when both said first engagement means and said lock means are employed, and in a second fixed relative orientation of said upper and lower ankle parts when both said second engagement means and said lock means are employed, and in a configuration allowing relative rotating of said upper and lower ankle parts with respect to each other when only said lock means is employed.

10. The ankle joint prosthesis of claim 9 wherein said rotation means comprises:
   a cam actuator having a cylindrical lateral end matching an inner diameter of said second eccentrically located hollow cylindrical portion and mounted therein, said cylindrical lateral end having a key thereon fitting a keyway inside said second eccentrically located hollow cylindrical portion, said cam actuator having a medial end;
   spring-loading means for holding said cam actuator inside said second eccentrically located hollow cylindrical portion under spring tension; and
   handle means on said medial end of said cam actuator for pulling said actuator in a medial direction and rotating said actuator.

11. The ankle joint prosthesis of claim 10 wherein said spring-loading means comprises:
   an end cap fitting over a lateral end of said lateral descending part, with a central through hole therein;

a helical spring;

a hollow sleeve inside said spring;

first and second washers disposed at first and second ends of said spring;

a screw passing through said central through-hole of said end cap, threaded through said first washer, said sleeve and spring, and said second washer, inserted into said cam actuator and screwed into a tapped central hole in said lateral end of said cam actuator;

wherein tightening or loosening of said screw adjusts a spring tension which holds said cam actuator against said medial descending part of said upper ankle part.

12. The ankle joint prosthesis of claim 10 wherein said handle means comprises a "D"-ring attached to said medial end of said cam actuator.

13. The ankle joint prosthesis of claim 9 wherein said lock means comprises:

a projection from a medial end face of said medial descending part of said upper ankle part;

wherein a medial end face of a cam actuator has first and second diametrically opposed holes each shaped complementarily to said projection, said holes being connected by a shallow semicircular slot in lateral end face of a central annular flange on said cam actuator, and said actuator can be rotated to position said projection in either of said diametrically opposed holes.

14. The ankle joint prosthesis of claim 9 wherein said first engagement means comprises:

a semicylindrical projection between said lateral and medial descending parts along an axis parallel to said coaxial through-holes; and a first semicylindrical slot complementary in shape to said semicylindrical projection, centrally located on said centered ascending part along an axis parallel to said through-hole in said lower ankle part;

wherein said upper ankle part engages said lower ankle part when said upper and lower parts are oriented at approximately 180° with respect to each other and a cam actuator is rotated fully clockwise for a left-ankle embodiment and fully counterclockwise for a right-ankle embodiment.

15. The ankle joint prosthesis of claim 9 wherein said second engagement means comprises:

a semicylindrical projection between said lateral and medial descending parts along an axis parallel to said coaxial through-holes; and a second semicylindrical slot complementary in shape to said semicylindrical projection, located approximately 75 to 90 degrees away from a first semicylindrical slot between said first slot and said base part of said lower ankle part along an axis parallel to said through-hole in said lower ankle part;

wherein said semicylindrical projection is engaged by said second semicylindrical slot when said upper and lower ankle parts are oriented at approximately 90 to 105 degrees with respect to each other and said cam actuator is rotated fully clockwise for a left-ankle embodiment and fully counterclockwise for a right-ankle embodiment.

16. The ankle joint prosthesis of claim 9 wherein said upper ankle part further comprises first attachment means for attaching said upper ankle part to said artificial leg and said lower ankle part further includes second attachment means for attaching said lower ankle part to said artificial foot.

17. The ankle joint prosthesis of claim 9 wherein said intermediate means includes hand-operable means for selecting said first fixed relative orientation, said second fixed relative orientation, or a condition of freedom of relative rotation between said upper and lower ankle parts.

* * * * *